(12) United States Patent
Rashid

(10) Patent No.: US 10,945,876 B2
(45) Date of Patent: Mar. 16, 2021

(54) FLUENCY AID

(71) Applicant: Cirrus Logic International Semiconductor Ltd., Edinburgh (GB)

(72) Inventor: Tahir Rashid, Tewkesbury (GB)

(73) Assignee: Cirrus Logic, Inc., Austin, TX (US)

( * ) Notice: Subject to any disclaimer, the term of this patent is extended or adjusted under 35 U.S.C. 154(b) by 154 days.

(21) Appl. No.: 16/259,093

(22) Filed: Jan. 28, 2019

(65) Prior Publication Data

US 2019/0231583 A1 Aug. 1, 2019

Related U.S. Application Data

(60) Provisional application No. 62/624,404, filed on Jan. 31, 2018.

(30) Foreign Application Priority Data

Mar. 15, 2018 (GB) ...................................... 1804159

(51) Int. Cl.
| | | |
|---|---|---|
| *A61F 5/58* | (2006.01) | |
| *G10L 21/0208* | (2013.01) | |
| *G06F 3/16* | (2006.01) | |
| *G09B 5/04* | (2006.01) | |
| *G10L 25/78* | (2013.01) | |
| *G09B 19/04* | (2006.01) | |
| *G10L 15/24* | (2013.01) | |
| *G10L 21/00* | (2013.01) | |
| *G06K 9/00* | (2006.01) | |
| *G10L 15/19* | (2013.01) | |

(52) U.S. Cl.
CPC ................ *A61F 5/58* (2013.01); *G06F 3/167* (2013.01); *G09B 5/04* (2013.01); *G10L 21/0208* (2013.01); *G06K 9/00335* (2013.01); *G09B 19/04* (2013.01); *G10L 15/19* (2013.01); *G10L 15/24* (2013.01); *G10L 21/00* (2013.01); *G10L 2025/783* (2013.01)

(58) Field of Classification Search
CPC .................................... A61F 5/58; A61B 5/12
USPC ........................................................... 600/23
See application file for complete search history.

(56) References Cited

U.S. PATENT DOCUMENTS 3,773,032 A 11/1973 Donovan et al.
5,794,203 A 8/1998 Kehoe et al.

FOREIGN PATENT DOCUMENTS

WO 2007005582 A1 1/2007

OTHER PUBLICATIONS

Combined Search and Examination Report under Sections 17 and 18(3), UKIPO, Application No. GB1804159.0, dated Sep. 14, 2018.

*Primary Examiner* — John P Lacyk
(74) *Attorney, Agent, or Firm* — Jackson Walker L.L.P.

(57) ABSTRACT

The present disclosure provides a fluency aid comprising: a masking signal generator; a switch operable to switch the masking signal generator between an ON state and an OFF state, wherein, when in the ON state, the masking signal generator is operable to generate a masking signal; a sound generator operable to receive the masking signal from the masking signal generator and generate a masking sound for output to a user of the fluency aid; and a voice detector operable to detect a voice of the user, wherein the masking signal generator is operable to generate the masking signal at least until the voice of the user is detected by the voice detector.

13 Claims, 3 Drawing Sheets

FLUENCY AID

The present disclosure claims priority to U.S. Provisional Patent Application Ser. No. 62/624,404, filed Jan. 31, 2018, and United Kingdom Patent Application No. 1804159.0, filed Mar. 15, 2018, each of which is incorporated by reference herein in its entirety.

TECHNICAL FIELD

The present disclosure relates to a fluency aid, and in particular to a fluency aid for use by persons suffering from a stammer or other speech-related conditions to aid fluency of speaking.

BACKGROUND

Stammering affects about 1-3% of the world's population. From historical records available it is suggested that the condition has always affected 1-3% of the population and is agnostic of race, religion, wealth, and upbringing. Many with the condition are misjudged by the way they talk and as a result many are treated differently in society and may fail to fulfil their potential. The situation can be particularly difficult for children and young adults who may be bullied or ridiculed at school and may find themselves withdrawing from society at a time when they should be finding their place in the world. The condition leaves many feeling anxious and isolated.

There are a number of known auditory effects that can help alleviate stammering. Electronic devices have in the past been created to utilise these effects to help give stammerers greater fluency. Many of these devices are large and cumbersome and cannot be used without attracting further ridicule. More discrete devices available still resemble medical devices and their cost puts them out of the reach of most stammerers.

Stammering and stuttering refer to the same condition, with the term stammer being used more in the UK and stutter being used more in the USA. The exact cause of stammering is unknown although it is now generally accepted that it is the result of the brain's neural circuits that control speech having been 'mis-wired'.

Some traditional forms of therapy work on many stammerers, but rely on the feedback from the user's speech and do not help, for example, if the user blocks or stammers on the first word. Some stammerers have trouble when starting to talk (starting to say something). That is to say, some may not present symptoms of stammering once already talking, but tend to stammer on the first word or even the first sound. The present disclosure relates to a fluency aid which aims to mitigate this form of stammering.

STATEMENTS OF INVENTION

According to an example of a first aspect there is provided a fluency aid comprising: a masking signal generator; a switch operable to switch the masking signal generator between an ON state and an OFF state, wherein, when in the ON state, the masking signal generator is operable to generate a masking signal; a sound generator operable to receive the masking signal from the masking signal generator and generate a masking sound for output to a user of the fluency aid; and a voice detector operable to detect a voice of the user, wherein the masking signal generator is operable to generate the masking signal at least until the voice of the user is detected by the voice detector.

When a person wishes to speak, but suffers from the type of stammering that occurs when the person starts talking, the fluency aid as described above may be used by operating the switch, so that the masking signal generator is switched to the ON state and produces a masking signal. The switch may be any suitable switch for this purpose. The masking signal is output from the masking signal generator. The masking signal is then input to a sound generator which, based on the masking signal, produces a masking sound. A masking sound may be any audible sound suitable for masking a user's own voice. For example, the masking sound may partially or completely obscure a user's voice from the user (from themselves), so that they cannot hear themselves speaking as clearly as they would normally. The masking sound is therefore played to the user once the masking signal generator is switched to the ON state.

In order that the user (stammerer) may begin speaking more readily and, beneficially, without stammering, the masking sound is played back until the user begins to speak. A voice detector is used to determine when the user begins to speak. Thus, the voice detector is operable to detect a user's voice i.e. sound signals that are indicative of speech. The masking signal that causes the masking sound to be emitted is therefore output until the voice detector detects the user's voice (i.e. signals that are indicative of voice or speech signals) so that the stammer may be reduced. It will be appreciated that the masking signal generator may be automatically switched to the OFF state upon detection of one or more speech signals by the voice detector, or a given time thereafter e.g. after a predetermined time interval has elapsed following the detection of one or more speech signals.

Examples of the present aspect are advantageous in that a user of the fluency aid who would otherwise suffer from blocking on the first word is able to speak more readily. Thus, the stammer may beneficially be reduced or even prevented entirely.

Preferably, the masking sound is faded out after the masking signal generator is switched to the ON state or following detection of the voice of the user.

In an example, the masking sound may be played (output) at an initial volume (loudness) which is reduced over time such that the masking sound becomes gradually quieter. This is advantageous to users who wish to hear the masking sound before beginning to speak, but who wish for the masking sound, and the masking effect, to be reduced over time. A user may therefore choose when to begin speaking based on a remaining volume of the masking sound. As the masking sound is faded, the masking effect becomes reduced. Therefore, a user may prefer to begin speaking when their own voice is only partially masked.

For some users, it may be preferable that the masking sound is played at a constant, initial volume, which is then gradually reduced once they have started speaking. Since some stammerers only stammer when starting to speak, once they have started speaking the masking sound may be reduced in volume so that they can hear their own voice again. This fading out of the masking sound, once the user begins speaking (once the voice detector detects a voice), allows the user to adjust the volume of their own voice, based on their own auditory feedback, so as to speak normally (at a normal volume).

According to one or more examples the fluency aid is further operable to emit a sound which is derived from the user's own voice. This is known as masked auditory feedback (MAF). MAF may be used in addition to the output masking sound described above, in that the masking signal may be combined with a voice signal representing the user's voice.

Thus, according to one or more examples of the present aspects the fluency aid is operable to derive a voice signal based on the user's own voice (which may have been detected by the voice detector), wherein the voice signal and the masking signal are combined to produce a masked auditory feedback, MAF, signal.

In other words, Masked Auditory Feedback (MAF) refers to the use of sound to mask the speaker's own voice. Thus, according to one or more example the masking sound is combined, by the fluency aid, with a signal derived from the detected voice signal. According to such examples the fluency aid may be able to feedback to the user a controlled feedback signal having a controllable amount of the voice signal and a controllable amount of the masking signal. In contrast to examples in which the fluency aid is not operable to feedback sound derived from the voice of the user, this method allows for greater control of what the user hears, as a MAF signal. In this case the MAF signal may be output to the sound generator to generate a MAF sound, based on the MAF signal.

In one example described above, the masking sound alone is output to the user, whereas in the example described involving MAF the fluency aid performs the MAF by providing MAF in combination with the provision of a masking signal. Thus, according to one or more examples the fluency aid is operable to combine the masking signal with a voice signal to produce a MAF signal, for output as MAF (a MAF sound). This is described in more detail below.

Preferably, the masking sound includes at least one of white noise, pink noise, tones and music.

The masking sound may take any suitable form, for example white noise, pink noise, tones and/or music. These forms of masking sound may be selected based on user preference, based on effectiveness at relieving the user from the symptoms of stammering or based on the situation, for example if the user needs to hear people that they are speaking to.

Preferably, the switch is a hook-switch, an electronic hook-switch and/or a user-operated switch.

A hook-switch or an electronic hook-switch are advantageous in that the user does not need to operate a switch themselves. For example, hook-switches are often found on telephones or headsets (headphones with a built-in microphone) and may switch on or off when a call is received, without separate user input. A user-operated switch is advantageous to give the user greater control over exactly when the masking sound is generated. These may be combined if, for example, the user wishes to make a call by a "hook-switch button".

In one example, the present disclosure may be embodied in noise cancelling headphones which include a hook-switch. To aid the user before speech has started the hook-switch is used to trigger generation of the masking signal which is output to the user. The hook-switch may be used to both enable and disable the masking or alternatively the hook-switch may be used to initiate the masking sound, which is then faded out as described above.

Preferably, the masking signal generator is switched to the OFF state through operation of the switch or after a predetermined time interval following operation of the switch.

A user may wish to control when the masking sound is stopped, rather than wait for it to fade out or otherwise. For example, if a user wishes to hear background sounds, the masking signal generator may be deactivated to allow this. The masking signal generator may also be deactivated when the switch remains in the ON state, but the masking sound has faded out sufficiently so as to be inaudible to the user. Preferably, once the masking signal generator is switched to the OFF state, the masking sound may be faded out rather than stopped abruptly.

According to one or more examples of the present aspects, the fluency aid may be further operable to provide an altered auditory feedback signal. Thus, according to one or more examples the fluency aid is operable to generate auditory feedback that has been altered in some way, such that the user perceives their speech differently from normal. Thus, according to one or more examples, the fluency aid further comprises a feedback signal generator for generating an additional altered auditory feedback, AAF, signal. It will be appreciated that the AAF signal can be considered to "trick" a user's brain in such a way as to aid the speech of the user and/or reduce the occurrence of stammering.

A user's brain can often quickly adapt to the "trick" being played on it, i.e. the effectiveness of the techniques used to increase fluency can be diminished over time. Therefore, it may in some circumstances be beneficial to combine multiple techniques to keep the brain from adapting and to further prolong the user's fluency. Thus, in at least one example, multiple techniques may be automatically applied at random so that the user's brain does not adapt so readily.

In addition to the masking sound generated by the sound generator, the fluency aid may further alter what is fed back to a user, by means of a feedback signal generator for generating an additional altered auditory feedback, AAF, signal. Additional Altered Auditory Feedback (AAF) may include for example: Masked Auditory Feedback (MAF); Delayed Auditory Feedback (DAF); and Frequency Altered Feedback (FAF).

In this case, for example, the voice detector is operable to output a voice signal, based on the detected voice, and the voice signal is altered by any of MAF, DAF and/or FAF, so as to produce an AAF signal, which is output to the sound generator. The sound generator then generates AAF (an AAF sound) to be output to a user. This may be in combination with the MAF described earlier.

Preferably, the additional altered auditory feedback, AAF, signal includes at least one of a delayed auditory feedback, DAF, signal and a frequency altered feedback, FAF, signal.

Delayed Auditory Feedback (DAF) refers to a technique whereby the speaker's voice is delayed before being presented to the speaker's ears. The level of improvement from stammering to fluency varies from user to user as does the long term effect. In cases where the user demonstrates a decreased effectiveness, altering the delay time has been reported to restore the effectiveness of DAF. The duration of the delay may for example lie in the range of 50-250 ms.

Frequency Altered Feedback (FAF) refers to a technique whereby the user's voice is shifted in frequency before being fed back to the user's ears. It is therefore also referred to as Frequency Shift Feedback (FSF). One approach is to shift the user's voice down one octave. The effectiveness of FAF on reducing stammering is similar to that of DAF. Some studies suggest FAF produces speech, closer to the user's normal speech, compared to MAF which tends to lead to louder speech and DAF which tends to lead to slower speech.

A combination of different forms of AAF provides an advantage of increased versatility and effectiveness to a broader range of stammerers and types of stammer.

According to one or more examples, the fluency aid may further comprise a pacing device to output an audible sound to the user at regularly timed intervals.

Speaking to a timed rhythm is another method of improving fluency in stammerers. There are many different approaches to speech therapy and if the stammerer is having therapy that relies on timing then this can be a valuable tool and may be used in combination with other forms of therapy.

According to an example of a second aspect there is provided a fluency aid comprising: a masking signal generator operable to generate a masking signal; and a switch, wherein the masking signal generator is operable, based on a state of a switch, to generate a masking signal, the masking signal being passed to a sound generator for generating a sound to a user of the fluency aid.

According to an example of a third aspect there is provided a fluency aid comprising: a switch operable to be switched between an ON state and an OFF state; a masking signal generator operable, based on a state of the switch, to generate a masking signal, wherein, when the switch is switched to the ON state, the masking signal generator is operable to begin generating the masking signal; a signal converter operable to receive the masking signal from the masking signal generator and convert the masking signal into a haptic output for output to a user of the fluency aid; and a voice detector operable to detect a voice of the user, wherein the masking signal generator is operable to generate the masking signal at least until the voice of the user is detected by the voice detector.

In an example, the user of a fluency aid may be provided with a masking sensory stimulus other than sound. A haptic output, such as a vibration or movement, providing a tactile sensation to the user is an alternative way to reduce stammering. Many stammerers require a stimulus, which may be a distraction, in order to reduce their tendency to stammer.

According to an example of a further aspect there is provided a telephone, headphones, acoustic noise cancelling headphones, smart watch, or other portable device comprising the fluency aid as described above. These and any other wearable devices may include a fluency aid as described above.

BRIEF DESCRIPTION OF DRAWINGS

For a better understanding of the present disclosure, and to show how the same may be carried into effect, reference will now be made, by way of example only, to the accompanying drawings in which.

Throughout this description any features which are similar to features in other figures have been given the same reference numerals.

DETAILED DESCRIPTION

The description below sets forth example fluency aids according to this disclosure. Further examples and implementations will be apparent to those having ordinary skill in the art. Further, those having ordinary skill in the art will recognize that various equivalent techniques may be applied in lieu of, or in conjunction with, the examples discussed below, and all such equivalents should be deemed as being encompassed by the present disclosure.

The arrangements described herein can be implemented in a wide range of devices and systems. However, for ease of explanation, an illustrative example will be described.

Figure 1:
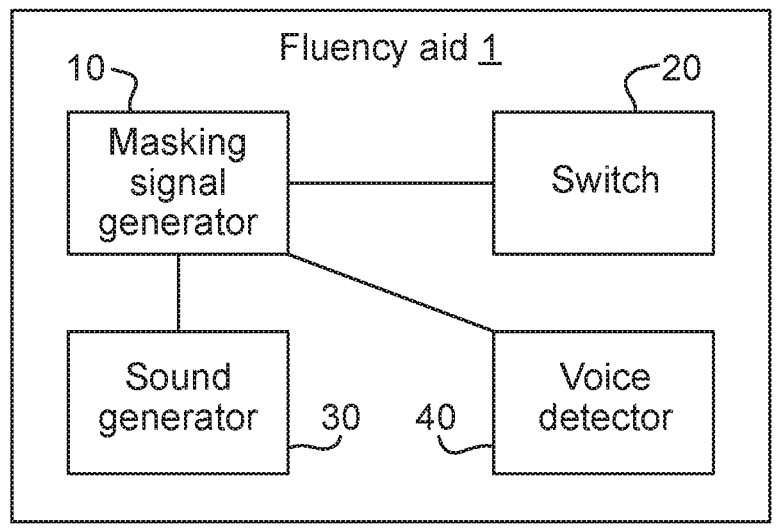
FIG. 1 is an example of a fluency aid according to the present disclosure.

FIG. 1 illustrates a first example of a fluency aid 1 according to the present disclosure. As shown, a fluency aid 1 includes a masking signal generator 10, a switch 20, a sound generator 30 and a voice detector 40.

The switch 20 is operable to switch the masking signal generator 10 between an ON state and an OFF state. The switch 20 may be any suitable form of switch. In one or more examples the switch 20 may be a hook-switch, an electronic hook-switch and/or a user-operated switch. The switch 20 may preferably have an ON and an OFF setting, corresponding to the ON state and an OFF state, respectively, of the masking signal generator 10 to indicate the state of the masking signal generator 10. The masking signal generator 10, when in an ON state, generates a masking signal. The masking signal is a signal generated by the masking signal generator 10 which is output from the masking signal generator 10 and input to a sound generator 30. The masking signal is a signal suitable for causing a sound generator 30 to generate a masking sound. The sound generator 30, upon receipt of the masking signal, generates a masking sound. The sound generator 30 may for example be a loudspeaker. The masking sound is then output from the sound generator such that, when the fluency aid is provided in an intended in-use configuration, the masking sound is audible to a user of the fluency aid 1. A voice detector 40 is arranged, in use, to detect a user's voice. For example, the voice detector 40 may be located close to a user's mouth or may be a microphone, such as a directional microphone, arranged to pick up a user's voice. The voice detector 40 may be a relatively basic microphone set up, or may be more sophisticated so as to be able to distinguish between a user's voice and another person's voice, so as to isolate the user's voice only.

The masking signal generator 10 generates a masking signal at least until the voice detector 40 detects that the user is talking. After the user begins talking the masking signal generator 10 may either continue to generate the masking signal or may cease to generate the masking signal such that the masking sound may continue or stop. According to one example, the masking sound may be gradually faded out.

The voice detector 40 may typically comprise a microphone. In addition, the voice detector may comprise signal processing operations which allow speech-like sounds to be identified. Thus, according to one example, sounds which are detected by the microphone of the voice detector will be converted into digital form for use by parts which implement digital signal processing operations upon signals that are derived from the microphone.

According to one or more examples the fluency aid is further operable to provide masked auditory feedback. Thus, in an example, the voice detector 40, in addition to being operable to detect sounds indicative of speech, may be further operable to output a voice signal, based on the detected voice. The voice signal and the masking signal may then be combined, for example by the sound generator 30 or a separate combiner, to produce a masked auditory feedback, MAF, signal. In order to improve the fluency assisting effect of this, or any, described example, the masking signal may be output to both of the user's ears. The masking sound may include, according to one or more examples, at least one of white noise, pink noise, tones and music.

In a further example, a user may wish to speak, for example to another person over the telephone or in person, and may find that unaided they have a tendency to experience stammering on the first sound of the first word. The user may therefore operate a fluency aid 1 as described above, by operating a switch 20, causing a masking sound to be produced. The fluency aid 1 outputs the masking sound, such as white noise, until the user starts speaking. This is preferably determined by the voice detector 40 which is able to detect sound. The voice detector 40 may operate on the basis of detecting any sound at all or any sound pressure level (SPL) above a threshold level (e.g. a threshold loudness level). Such a threshold may be calibrated based on detected background sound levels. Alternatively, the voice detector 40 may be operable to recognise sounds resembling speech, for example speech patterns, or even a specific user's voice so as to distinguish the user's voice from the voices of other people speaking nearby.

When determining whether the user has started speaking, the voice detector 40 may require that speech is detected, in any of the ways described above, for a minimum amount of time. A user of the fluency aid 1 may experience stammering at the first spoken word, but may still produce an initial sound. Therefore, it may be beneficial to require a minimum amount of speech (require a user to be speaking for a minimum amount of time) before considering a voice as detected. This minimum amount of speech may be set as a few seconds of continuous speech or, if the voice detector 40 is able to recognise sounds resembling speech, may be set as one or more spoken words.

The masking signal generator 10 is operable to continue generating the masking signal, which in turn leads to the masking sound being output, at least until the voice detector 40 detects the user's voice. Once the user starts speaking, and the voice detector 40 considers the speech to be a detected voice as described above, the masking signal generator 10 may either continue to generate the masking signal or may stop generating the masking signal.

A user may prefer that the masking sound is faded out (gradually reduced in output volume/loudness). For example, the masking sound may be initially output loud enough to completely mask the user's voice. If a user begins speaking without being able to hear their own voice, an initial stammer may be avoided and improved fluency can be achieved. Some users however may prefer that the masking sound is initially quite loud, but is gradually made quieter, either before they begin speaking or after.

In an example, the voice detector 40 is operable to output a voice signal, based on the user's voice, which may be combined, for example by the sound generator 30, with the masking signal to produce a masked auditory feedback, MAF, signal. The MAF signal may then be received or processed, by the sound generator 30, in order to generate a MAF sound corresponding to the MAF signal.

Figure 2:
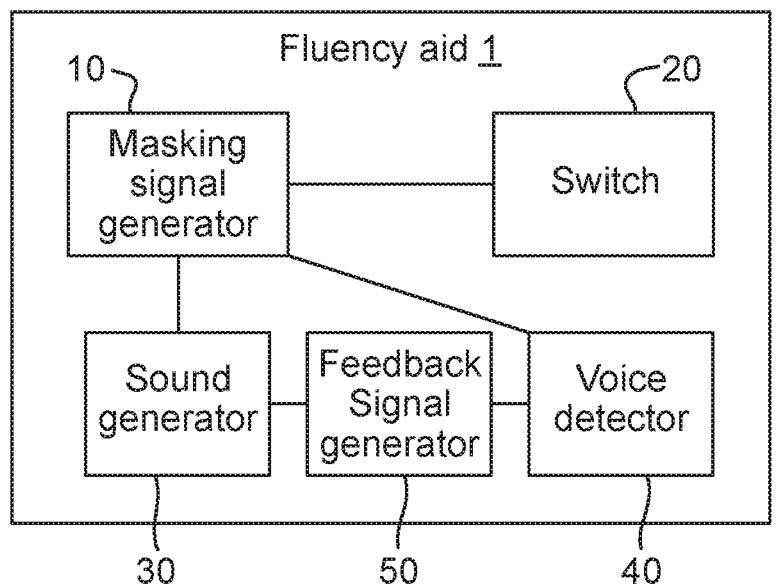
FIG. 2 is an example of a fluency aid according to the present disclosure further comprising a feedback signal generator.

FIG. 2 illustrates a second example of a fluency aid 1 according to the present disclosure, wherein the fluency aid 1 further includes a feedback signal generator 50 for generating an additional altered auditory feedback, AAF, signal. The feedback signal generator 50 generates the AAF signal based on a voice signal from the voice detector 40, which is altered for example by any of MAF, DAF and/or FAF. The AAF signal is then output to the sound generator 30, which generates the corresponding AAF sound.

In an example, in addition to a masking signal, for masking the user's own voice, it may be beneficial to apply altered auditory feedback AAF, such as DAF and/or FAF, as described above, to the voice signal detected by the voice detector 40.

In accordance with the example, the voice of the user, detected by the voice detector 40, may be output from the voice detector 40 as a voice signal. The feedback signal generator 50 is then operable to generate an AAF signal, based on the voice signal, wherein one or more types of AAF have been applied to the voice signal. The AAF signal may then be output to the sound generator 30 and, on the basis of the AAF signal, the sound generator 30 generates AAF (an AAF sound), which may be output to the user.

Figure 3:
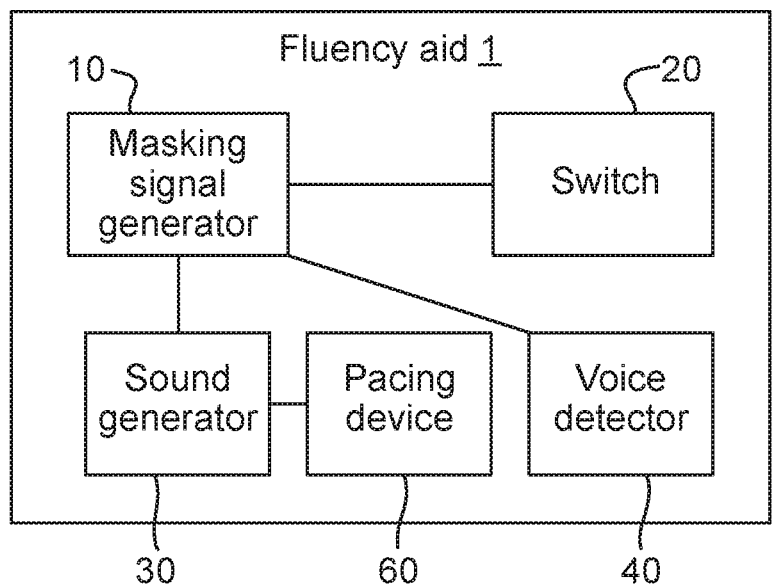
FIG. 3 is an example of a fluency aid according to the present disclosure further comprising a pacing device.

FIG. 3 illustrates a third example of a fluency aid 1 according to the present disclosure, wherein the fluency aid 1 further includes a pacing device (pacing signal generator) 60 to output an audible sound to the user at regularly timed intervals. The pacing device 60 may be included in, or provided separately from, the sound generator 30. The pacing device 60 provides the user with an audible rhythm with which to time their speech.

Speaking to a timed rhythm is another method of improving fluency in stammerers. There are many different approaches to speech therapy and if the stammerer shows benefit from therapy that relies on timing then this can be a valuable tool and may be used in combination with other forms of therapy. Users of the fluency aid may prefer specific sounds to which to time their speech. A click or tone provides a clear regular beat, easily recognisable among other sounds.

In an example, the fluency aid 1, including the pacing device 60, may be used by a stammerer who has found that speaking in time with a regular beat aids fluency of speech. The pacing device 60 is operable to output the regular beat, which is an example of an audible sound, as described above. The pacing device 60 may be activated and deactivated by the switch 20 in a similar manner to the masking signal generator 10. That is to say, the switch 20, which is operable to switch the masking signal generator 10 between an ON state and an OFF state, is also operable to switch the pacing device 60 between an ON state and an OFF state, such that the masking signal generator 10 and the pacing device 60 are switched on (switched to an ON state) and off (switched to an OFF state) together.

Although not shown in the figures, the skilled person will appreciate that a fluency aid according to at least one example may include both a feedback signal generator 50 as in the second example as well as a pacing device 60 as in the third example.

Figure 4:
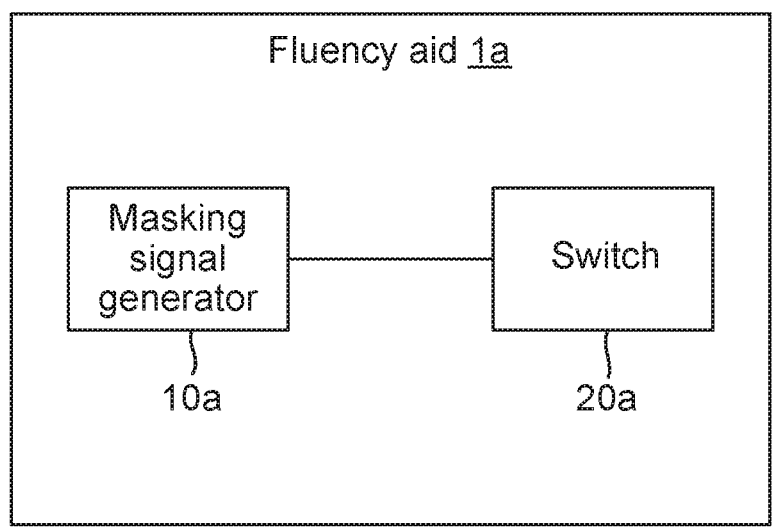
FIG. 4 is another example of a fluency aid according to the present disclosure.

FIG. 4 illustrates a fourth example of a fluency aid 1a according to the present disclosure. As shown, the fluency aid 1a comprises a masking signal generator 10a and a switch 20a. The switch 20a switches between states and, based on the state of the switch 20a, the masking signal generator 10a generates a masking signal. The masking signal may then be passed to a sound generator, external of the fluency aid 1a, for generating a sound to a user of the fluency aid 1a.

Masking sounds can aid fluency in many stammerers. Depending on the type and output volume (loudness) of the masking sound, it may be beneficial to have control over the masking sound generation based on the state of a switch. Therefore, a user of the fluency aid 1a may have greater control over the exact times when the masking sound is generated.

In an example, the masking signal generator 10a may be switched to the OFF state through operation of the switch 20a or after a predetermined time interval following operation of the switch 20a. A user may wish to control when the masking sound is stopped, rather than wait for it to fade out or otherwise. For example, if a user wishes to hear background sounds, the masking signal generator 10a may be deactivated to allow this. The masking signal generator 10a may also be deactivated when the switch remains in the ON state, but the masking sound has faded out sufficiently so as to be inaudible to the user. In another example, once the masking signal generator 10a is switched to the OFF state, the masking sound may be faded out rather than stopped abruptly.

Figure 5:
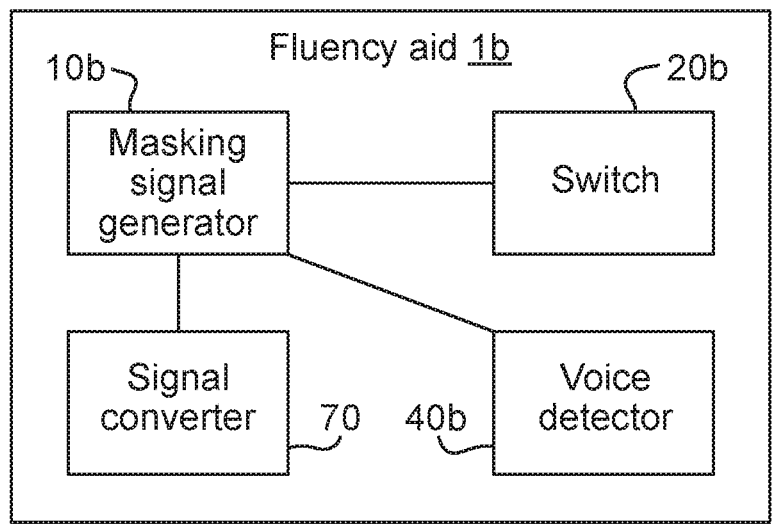
FIG. 5 is an example of a fluency aid according to the present disclosure comprising a signal converter.

FIG. 5 illustrates a fifth example of a fluency aid 1b according to the present disclosure. The fluency aid 1b of FIG. 5 operates similarly to the fluency aid 1 of FIG. 1, except that the sound generator 30 is not included and, instead, the fluency aid 1b includes a signal converter 70. The signal converter 70 receives a masking signal from the masking signal generator 10b and converts the masking signal into a haptic output for output to a user of the fluency aid. Haptic output may include any form of tactile stimulus output to a user. Haptic output may either obscure the user's own voice or provide a distraction, thus masking the user's own voice by redirecting the user's concentration.

Any of the above-described examples may be included in a telephone, headphones, acoustic noise cancelling headphones, smart watch, or other portable or wearable device.

It will be appreciated that features of any of the above aspects and examples may be provided in any combination with the features of any other of the above aspects and examples.

Examples may further be implemented in a host device, especially a portable and/or battery powered host device such as a mobile computing device for example a mobile telephone or smartphone.

The fluency aid may be at least partly implemented within a speaker housing. The housing may be, e.g. that of a wired or wireless headset, an ear-bud, a supra-aural head phone or a speaker portion of a mobile device such as a mobile phone handset. Thus, the housing may comprise parts associated with the masking signal generator, the sound generator (e.g. at least one speaker configured to receive the masking signal generator and to output a masking sound), the switch and the voice detector (e.g. mic plus associated processing). Alternatively, the parts associated with one or more features of the fluency aid may be provided in an apparatus separate to the apparatus that comprises the at least one speaker (sound generator). For example, the fluency aid may be at least partly implemented within a mobile handset or a "dongle", wherein a wired or wireless connection is provided between the apparatuses. According to one implementation the switch and/or the voice detector are provided in an apparatus that is separate from the apparatus, e.g. headset or ear-bud.

It should be noted that the above-mentioned examples illustrate rather than limit the disclosure, and that those skilled in the art will be able to design many alternative configurations without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope. The features of any dependent claim may be combined with the features of any of the independent claims or other dependent claims.

The invention claimed is:

1. A fluency aid comprising:
a masking signal generator;
a switch operable to switch the masking signal generator between an ON state and an OFF state, wherein, when in the ON state, the masking signal generator is operable to generate a masking signal;
a sound generator operable to receive the masking signal from the masking signal generator and generate a masking sound for output to a user of the fluency aid; and
a voice detector operable to detect a voice of the user, wherein the masking signal generator is operable to generate the masking signal at least until the voice of the user is detected by the voice detector;
wherein the masking sound is faded out after the masking signal generator is switched to the ON state or following detection of the voice of the user.

2. The fluency aid according to claim 1, wherein the voice detector is operable to output a voice signal, based on the detected voice, and wherein the voice signal and the masking signal are combined to produce a masked auditory feedback, MAF, signal.

3. The fluency aid according to claim 1, wherein the masking sound includes at least one of white noise, pink noise, tones and music.

4. The fluency aid according to claim 1, wherein the switch is a hook-switch, an electronic hook-switch and/or a user-operated switch.

5. The fluency aid according to claim 1, wherein the masking signal generator is operable to be switched to the OFF state by operation of the switch.

6. The fluency aid according to claim 1, further comprising:
a feedback signal generator for generating an altered auditory feedback, AAF, signal.

7. The fluency aid according to claim 6, wherein the altered auditory feedback, AAF, signal includes at least one of a delayed auditory feedback, DAF, signal and a frequency altered feedback, FAF, signal.

8. The fluency aid according to claim 1, further comprising:
a pacing device to output an audible sound to the user at regularly timed intervals.

9. A fluency aid comprising:
a masking signal generator operable to generate a masking signal; and
a switch;
wherein the masking signal generator is operable, based on a state of the switch, to generate the masking signal, the masking signal being passed to a sound generator for generating a masking sound;
wherein the masking sound is faded out after the switch is switched to an ON state or following detection of a voice of a user.

10. A fluency aid comprising:
a switch operable to be switched between an ON state and an OFF state;
a masking signal generator operable, based on a state of the switch, to generate a masking signal, wherein, when the switch is switched to the ON state, the masking signal generator is operable to begin generating the masking signal;

a signal converter operable to receive the masking signal from the masking signal generator and convert the masking signal into a haptic signal for output to a user of the fluency aid; and a voice detector operable to detect a voice of the user, wherein the masking signal generator is operable to generate the masking signal at least until the voice of the user is detected by the voice detector;

wherein the haptic signal is faded out after the switch is switched to the ON state or following detection of the voice of the user.

11. A telephone, headphones, acoustic noise cancelling headphones, smart watch, or other portable device comprising the fluency aid according to claim 1.

12. A telephone, headphones, acoustic noise cancelling headphones, smart watch, or other portable device comprising the fluency aid according to claim 9.

13. A telephone, headphones, acoustic noise cancelling headphones, smart watch, or other portable device comprising the fluency aid according to claim 10.

* * * * *